(12) United States Patent
Judd et al.

(10) Patent No.: US 8,167,837 B2
(45) Date of Patent: *May 1, 2012

(54) CONTROLLED RETRACTION SYRINGE AND PLUNGER THEREFOR

(75) Inventors: Damien Judd, Heathmont (AU); Joseph Hermes Kaal, Morpeth (AU); Craig Stephen Thorley, Largs (AU)

(73) Assignee: Unitract Syringe Pty Ltd., Sydney, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/911,481

(22) PCT Filed: Apr. 18, 2006

(86) PCT No.: PCT/AU2006/000516
§ 371 (c)(1),
(2), (4) Date: Sep. 22, 2008

(87) PCT Pub. No.: WO2006/108243
PCT Pub. Date: Oct. 19, 2006

(65) Prior Publication Data
US 2009/0093759 A1    Apr. 9, 2009

(30) Foreign Application Priority Data

Apr. 15, 2005   (AU) ............................... 2005901892
Apr. 15, 2005   (AU) ............................... 2005901893
Dec. 2, 2005    (AU) ............................... 2005906768

(51) Int. Cl.
*A61M 5/00*   (2006.01)
*A61M 1/00*   (2006.01)
*A61M 5/32*   (2006.01)

(52) U.S. Cl. ..................... 604/110; 604/220; 604/195

(58) Field of Classification Search .......... 640/110, 640/187, 195–196, 220; 604/110, 187, 195–196, 604/220
See application file for complete search history.

(56) References Cited

U.S. PATENT DOCUMENTS

| 4,581,022 | A | * | 4/1986 | Leonard et al. | 604/229 |
| 5,098,402 | A | | 3/1992 | Davis | |
| 5,112,307 | A | * | 5/1992 | Haber et al. | 604/110 |
| 5,114,404 | A | * | 5/1992 | Paxton et al. | 604/110 |
| 5,190,526 | A | * | 3/1993 | Murray et al. | 604/110 |

(Continued)

FOREIGN PATENT DOCUMENTS
WO    94/04207 A1   3/1994
(Continued)

*Primary Examiner* — Nicholas Lucchesi
*Assistant Examiner* — Rebecca E Eisenberg
(74) *Attorney, Agent, or Firm* — LeClairRyan, a Professional Corporation

(57) ABSTRACT

A retractable syringe (11) and plunger (20) therefore are provided, whereby the plunger comprises a controlling means (62) which facilitates control of the rate of retraction of the retractable needle. By controlling the rate of needle retraction, the likelihood of blood spattering is reduced, thereby improving the user-friendliness and appeal of the retractable syringe. Typically, the syringe is a prefilled syringe. Following plunger depression, a symmetrical ejector member (92) releases the retractable needle (40) from a retaining member (30) to thereby allow retraction of the retractable needle. Needle retraction is facilitated by a biasing means (70), such as a spring or other compressible and/or de-compressible device. The plunger comprises a plunger housing (21), in which is located the controlling means. The controlling means may be a pneumatic air space (324) inside the plunger housing which automatically acts against the retracting needle to thereby control or regulate the rate of retraction.

22 Claims, 18 Drawing Sheets

U.S. PATENT DOCUMENTS

| | | |
|---|---|---|
| 5,211,628 A | 5/1993 | Marshall |
| 5,215,533 A * | 6/1993 | Robb .......................... 604/195 |
| 5,498,244 A * | 3/1996 | Eck ............................. 604/198 |
| 5,531,694 A * | 7/1996 | Clemens et al. ............. 604/110 |
| 5,681,292 A * | 10/1997 | Tober et al. ................. 604/195 |
| 5,702,367 A | 12/1997 | Cover et al. |
| 5,882,342 A * | 3/1999 | Cooper et al. ............... 604/195 |
| 6,050,977 A | 4/2000 | Adams |
| 6,090,078 A | 7/2000 | Erskine |
| 6,235,003 B1 * | 5/2001 | Dysarz ......................... 604/195 |
| 6,706,019 B1 | 3/2004 | Parker et al. |
| 2004/0030294 A1 * | 2/2004 | Mahurkar ..................... 604/192 |
| 2004/0215150 A1 | 10/2004 | Shue et al. |
| 2005/0096604 A1 * | 5/2005 | Maggioni ..................... 604/240 |
| 2005/0177100 A1 * | 8/2005 | Harper et al. ................ 604/89 |
| 2006/0069348 A1 | 3/2006 | Parker et al. |
| 2006/0129096 A1 | 6/2006 | Wright |

FOREIGN PATENT DOCUMENTS

| | | |
|---|---|---|
| WO | 00/18466 A1 | 4/2000 |
| WO | 01/51107 A1 | 7/2001 |

* cited by examiner

CONTROLLED RETRACTION SYRINGE AND PLUNGER THEREFOR

This application is a national stage application under 35 U.S.C. §371 of PCT/AU2006/000516, filed Apr. 18, 2006, which claims the benefit of Australian Patent Application Nos. 2005901892, filed Apr. 15, 2005; 2005901893, filed Apr. 15, 2005; and 2005906768, filed Dec. 2, 2005, all of which are hereby incorporated by reference in their entirety.

FIELD OF THE INVENTION

THIS INVENTION relates to syringes. More particularly, this invention relates to a retractable syringe that includes a needle retraction mechanism to prevent re-use of the syringe, wherein the needle retraction mechanism acts in a controlled manner.

BACKGROUND OF THE INVENTION

The practice of sharing syringes without adequate sterilization between successive users is a major contributor to the transfer of Human Immunodeficiency Virus (HIV) and Hepatitis with subsequent severe repercussions for the sufferer and at a high cost to society for supporting and providing medical attention to sufferers.

In response to this problem, syringes have been developed with the aim of preventing syringe re-use.

One solution has been to develop syringes where the needle is permanently retractable into the barrel of the syringe, retraction driven by a compressed spring, as for example described in International Publication WO 01/80930. An improved "feel" may be provided for a syringe user such as by incorporating a pre-compressed retraction spring that provides minimal resistance to plunger depression, as described in International Publication WO 2004/082747.

However, generally spring decompression is relatively uncontrolled, which in use can lead to excessively forceful needle retraction that can result in blood splattering as air is forced from the syringe barrel as the needle retracts into the barrel.

SUMMARY OF THE INVENTION

The present invention appreciates the need to make retractable syringes as "user friendly" and appealing as possible, while not compromising the safety features provided by the syringe.

The present invention is therefore broadly directed to a retractable syringe which comprises a mechanism to facilitate needle retraction in a controlled or regulated manner.

Preferably, in use the retractable syringe reduces or minimizes blood splattering associated with needle retraction.

A preferred form of the invention relates to a syringe having a removable controlling means, or component thereof, which does not contact fluid contents of the syringe and which therefore may be discarded as "clean" waste, thereby leaving only a contaminated portion of the syringe for waste disposal.

In a particularly preferred form, the retractable syringe is a prefilled syringe.

In a first aspect, the invention provides a plunger for a syringe having a retractable needle, said plunger comprising a controlling means which facilitates control of the rate of retraction of said retractable needle when engaged with said plunger.

In a second aspect, the invention provides a syringe having a barrel, a retractable needle and a plunger engageable with said retractable needle, said plunger comprising a controlling means which facilitates control of the rate of retraction of said retractable needle when engaged with said plunger.

Suitably, retraction of said retractable needle is facilitated by a biasing means, such as a spring or other compressible and/or de-compressible device.

Preferably, said spring is initially compressed so that decompression of said spring facilitates retraction of said retractable needle.

Preferably, said plunger comprises a plunger housing, said controlling means being initially located at least partly within said plunger housing.

In one particular embodiment, the controlling means comprises a control member operable by a syringe user.

In a particular form of this embodiment, said plunger further comprises a plunger member releasably engaged with said control member, which is initially at least partly within the plunger housing, arranged so that following retraction of said plunger said control member may be disengaged from said plunger member.

In another particular embodiment, the controlling means is a pneumatic controlling means.

In a particular form of this embodiment, said plunger further comprises a first plunger member and a second plunger member and a plunger housing, which co-operate to form said pneumatic controlling means.

In one particular form, said syringe further comprises a retaining member that facilitates initial retention of said retractable needle at a needle end of said barrel.

Preferably, said syringe further comprises an ejector member, said ejector member operable to release said retractable needle from said retaining member to thereby allow retraction of said retractable needle when delivery of fluid contents of said syringe is complete.

Preferably, said ejector member does not require alignment with said retaining member to release said retractable needle from said retaining member.

In particular embodiments, said ejector member is annular, ring-like or of any other generally symmetrical shape.

In a preferred embodiment, said syringe further comprises a sealing means that comprises an inner sealing member and an outer sealing member.

Preferably, said inner sealing member has a tapered cross section and comprises a plurality of annular steps that releasably engage complementary annular ribs inside said outer sealing member.

In one particular embodiment, said retractable needle comprises a cannula and a needle body.

Preferably, said needle body has a tapered cross section, tapering toward said cannula, and comprises a plurality of steps.

Preferably, said needle body is mounted to a needle mount located in said barrel.

Preferably, said a needle mount comprises a plurality of complementary steps that respectively, releasably receive or engage said plurality of steps of said needle body.

From the foregoing it will also be appreciated that in other aspects the invention also relates to a method of assembly of the aforementioned plunger and/or syringe and to a method of use of the aforementioned syringe.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein.

DETAILED DESCRIPTION OF THE PREFERRED EMBODIMENT

Figure 1:
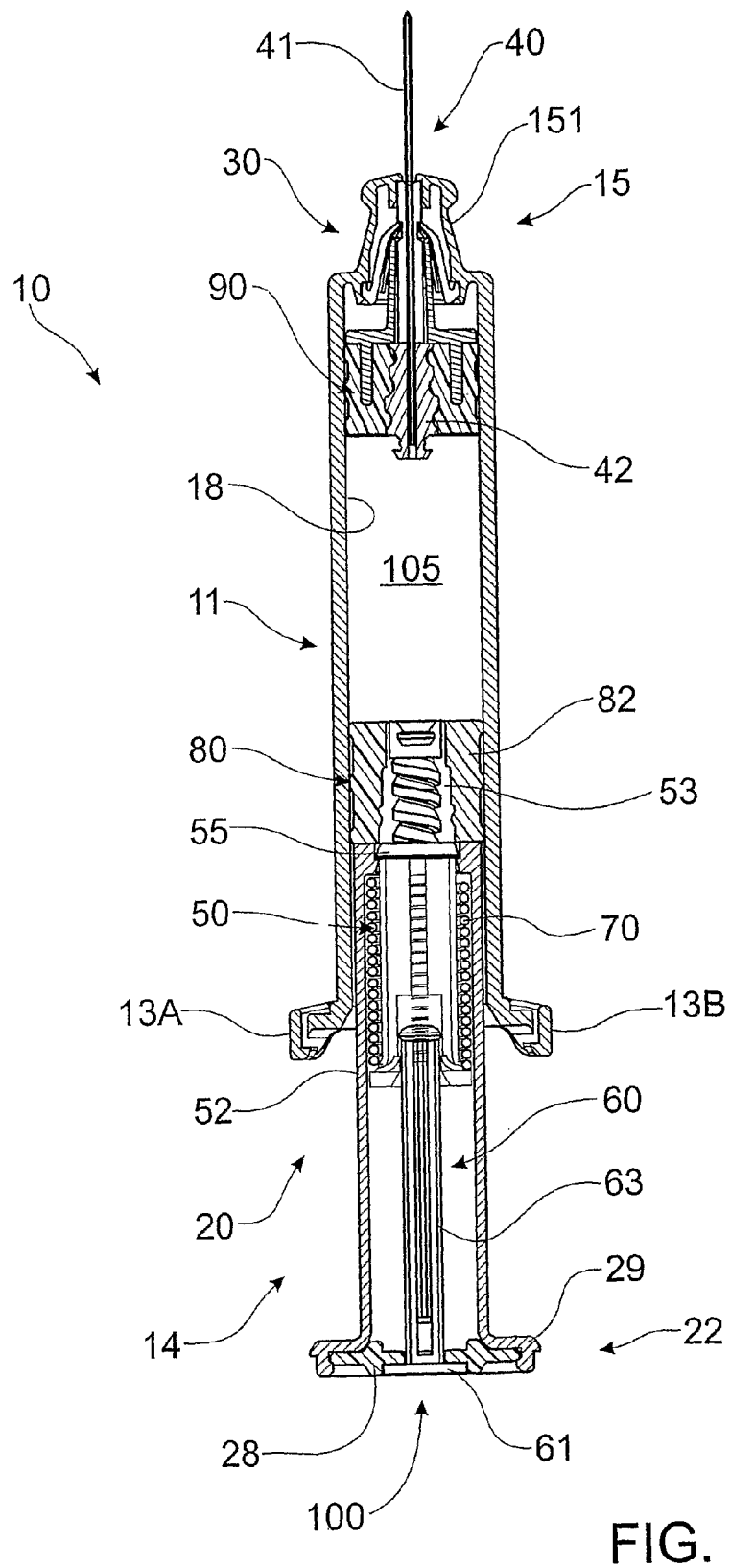
FIG. 1 is a sectional view of an embodiment of a retractable syringe.
Figure 2:
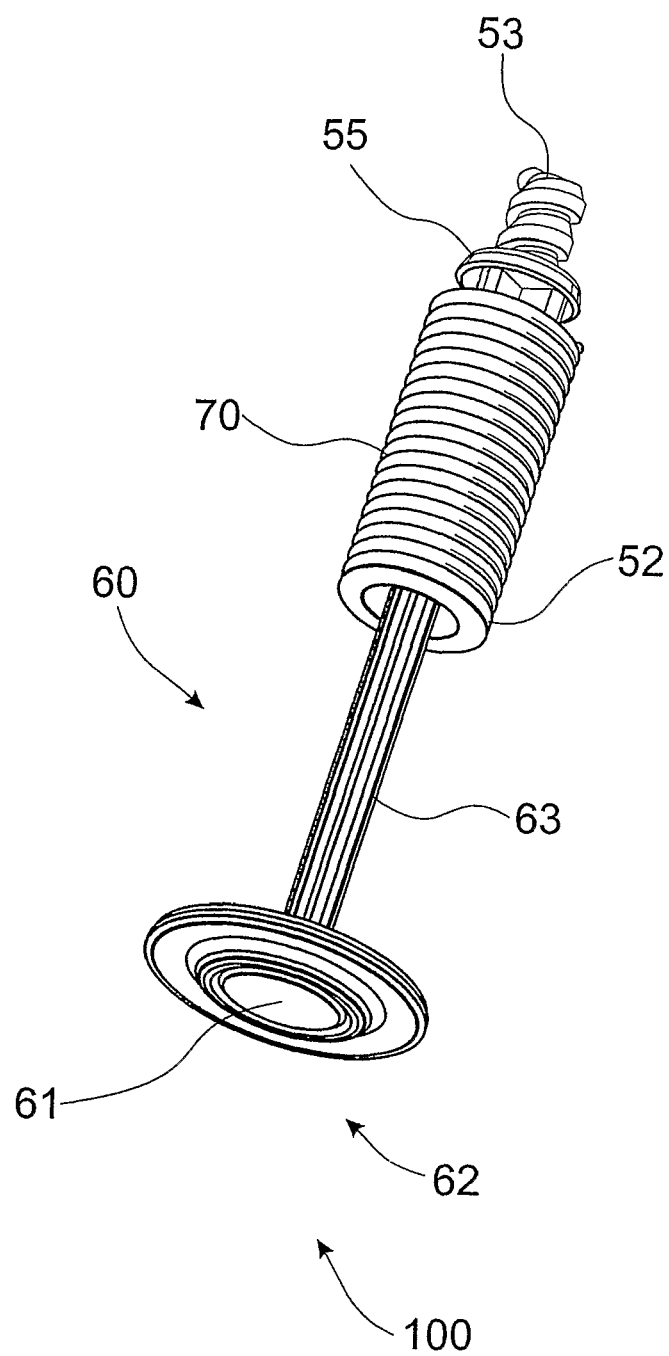
FIG. 2 is a perspective view of an embodiment of a plunger.

Referring to FIG. 1 and FIG. 2, an embodiment of syringe 10 comprises barrel 11 and plunger 20 having sealing means 80 mounted to plunger 20. Barrel 11 comprises plunger end 14 at which are located finger grips 13A, 13B, and needle end 15 having domed portion 151 onto which can be mounted a sheath or other protective cover for cannula 41 (not shown). Inside domed portion 151 is mounted retaining member 30, a needle mount in the form of needle seal 90 and retractable needle 40 that comprises cannula 41 and retractable needle body 42. Mounting of retaining member 30 inside needle end 15 of barrel 11 will be described more clearly with reference to FIG. 5.

Barrel 11 further comprises inside wall 18 which, together with needle seal 90 and plunger seal 80 define fluid space 105 inside barrel 11. In use, plunger 20 is movable axially into fluid space 105 to facilitate delivery of fluid contents of syringe 10. In a preferred embodiment, fluid space 105 is prefilled with the fluid contents to be delivered by syringe 10.

Figure 3:
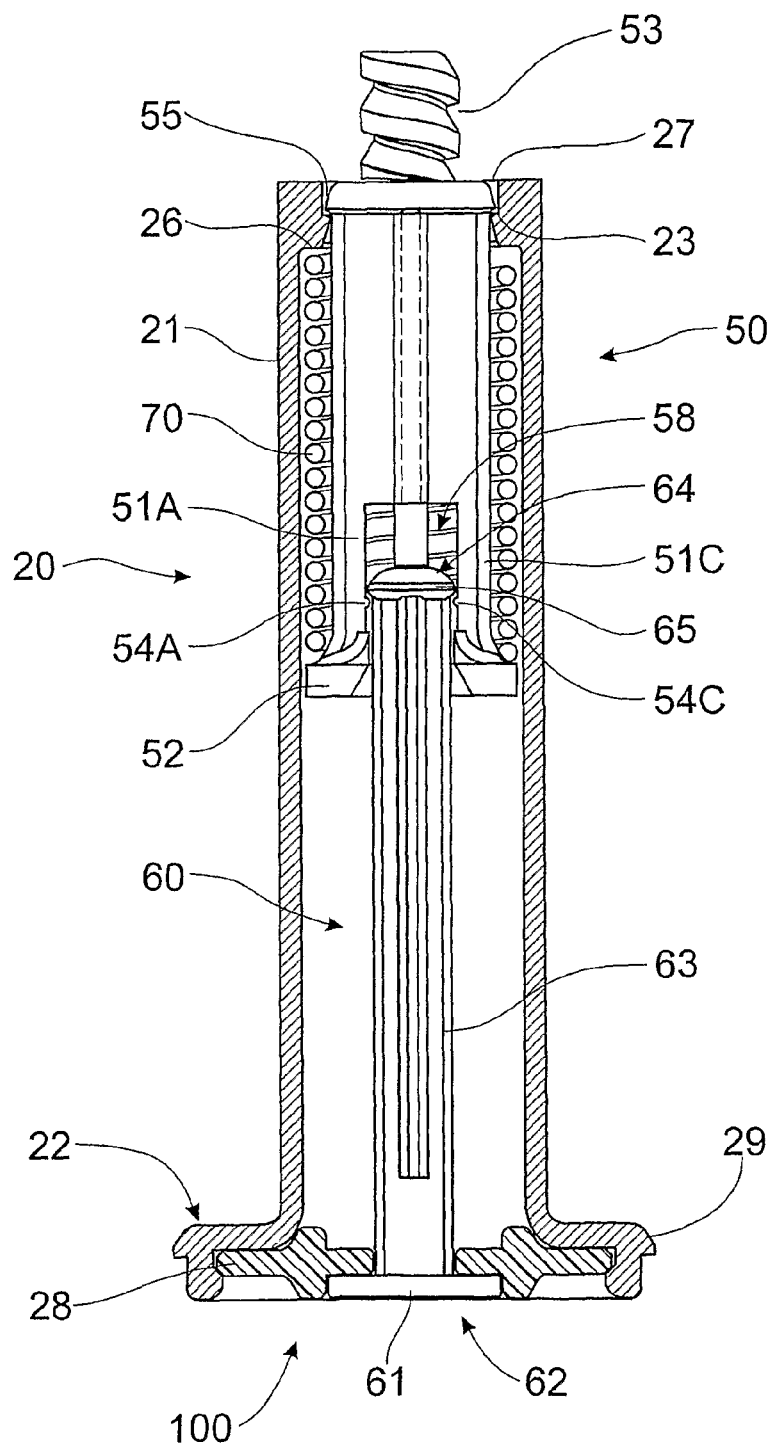
FIG. 3 is a sectional view of an embodiment of a plunger.

Referring particularly to FIG. 2 and FIG. 3, plunger 20 comprises plunger housing 21 and button 22 with flanged rim 29 operable by a user, plunger member 50 and compressed spring 70. Inside housing 21 is located plunger member 50 and control rod 60. Control rod 60 has shaft 63 and button 61 which co-operates with plug member 28 and flanged rim 29 of plunger housing 21 to form control member 62 of controlling means 100 operable by a user.

Plunger member 50 comprises vanes 51A, 51B, 51C, 51D (51B, 51D not shown) that terminate at annular base 52, thereby defining cavity 58 that accommodates ribbed member 64 of control rod 60. Vanes 51A, 51B, 51C, 51D respectively comprise nub 54A, 54B, 54C, 54D (54B, D not shown), that at least temporarily prevent travel of ribbed member 64 toward plunger end 14 of syringe 10, by bearing against lip 65 of ribbed member 64.

First plunger member 50 further comprises projection 53, which in this embodiment is screw threaded, and rim 55 distal to annular base 52. When assembled, rim 55 fits into recess 27 of plunger housing 21 by way of an interference fit to aperture ledge 23 so that compressed spring 70 cannot force first plunger member 50 out of engagement with plunger housing 21.

Biasing means 70, in this embodiment a compressed spring, is mounted to first plunger member 50, held in a compressed state between annular base 52 of plunger member 50 and circumferential shoulder 26 of plunger housing 21.

Figure 4:
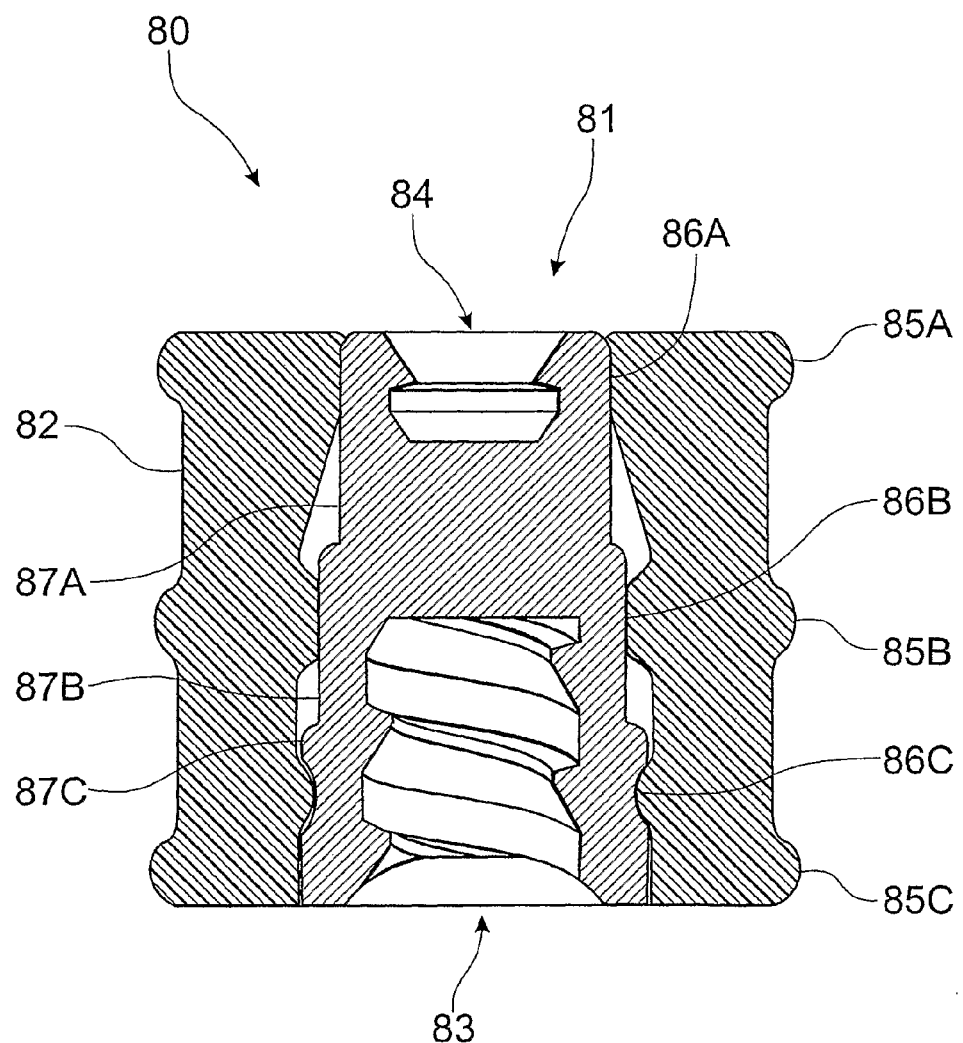
FIG. 4 is a sectional view of an embodiment of a sealing means wherein an inner sealing member is suitable for screw-threaded engagement with a plunger member.

Referring now to FIG. 3 and FIG. 4, the interaction between plunger 20 and plunger seal 80 may be better understood.

Plunger seal 80 comprising inner seal member 81 and outer seal member 82 is mounted to plunger 20 to thereby provide a fluid seal between plunger 20 and barrel 11.

Projection 53 of plunger member 50 projects from recess 27 of plunger housing 21 toward needle end 15 of barrel 11 and is coupled to inner seal member 81 by way of plunger engaging means 83 in the form of a complementary screw thread in inner seal member 81.

Figure 5:
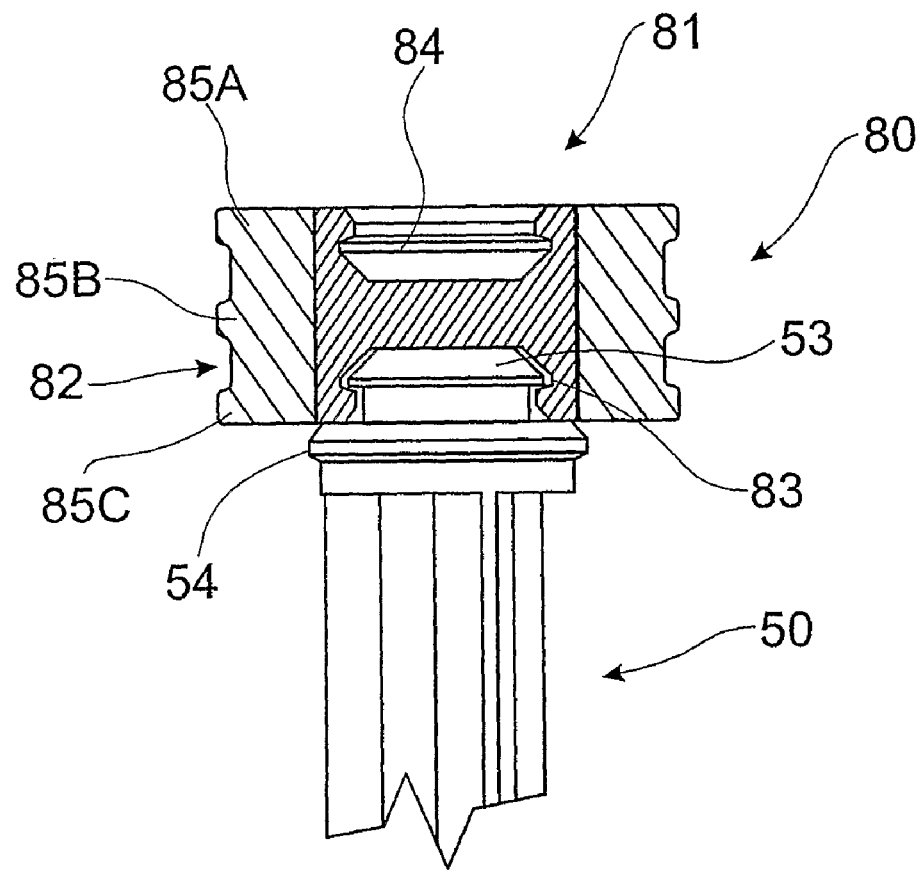
FIG. 5 is a sectional view of an alternative embodiment of a sealing means and plunger showing snap-lock engagement.

In an alternative embodiment shown in FIG. 5, plunger engaging means 83 may be in the form of snap lock recess 83 that engages snap-lock projection 53 on plunger member 50, rather than a complementary screw thread.

Figure 6:
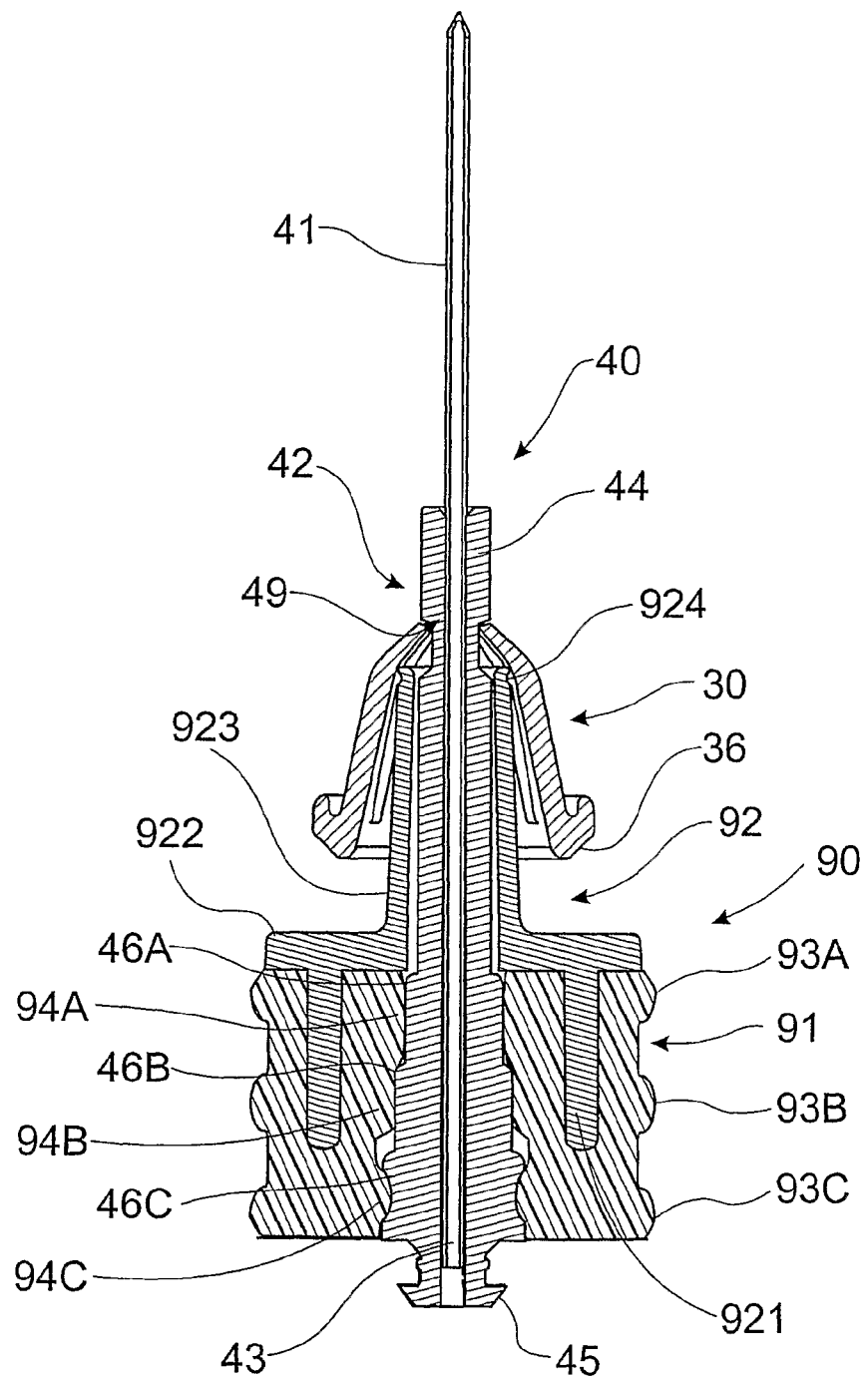
FIG. 6 is a sectional view of an embodiment of a needle seal, retractable needle and a retaining member.

Referring to FIG. 4 and FIG. 6, outer seal member 82 comprises body 84 and circumferential ribs 85A, B, C that effect a fluid-tight seal between plunger 20 and inside wall 18 of barrel 11.

It will also be appreciated from FIG. 4 in contrast to FIG. 5, that inner seal member 81 may have a tapered cross section and comprise plurality of annular steps 87A, 87B, 87C that engage complementary annular ribs 86A, 86B, 86C inside outer seal member 82. This stepped configuration means that the amount of movement required to dislodge inner seal member 81 from outer seal member 82 is minimized. Resistance to withdrawal of inner seal member 81 from outer seal member 82 effectively reduces as cross-sectionally tapered inner seal member 81 is withdrawn.

Inner seal member 81 further comprises recessed seat 84 that receives lip 45 of retractable needle body 42 towards the end of plunger 20 depression prior to retraction of retractable needle 40, as will be understood by referring to FIG. 6.

At needle end 15 of barrel 11 is located retractable needle 40 and needle seal 90 that comprises sealing body 91 and ejector member 92 fitted into sealing body 91.

Retractable needle 40 comprises cannula 41 mounted to body 42. Cannula 41 communicates with fluid contents in fluid space 105 of barrel 11 by way of bore 43 in needle body 42. It is advantageous for retractable needle body 42 to have a tapered cross section, tapering toward cannula 41, and comprise plurality of steps 46A, 46B, 46C. As evident from FIG. 6, sealing body 91 comprises plurality of complementary steps 94A, 94B, 94C that respectively receive steps 46A, 46B, 46C of retractable needle body 42.

This stepped configuration means that the amount of movement required to dislodge retractable needle 40 from needle seal 90 is minimized. The taper assists withdrawal of retractable needle 40 from needle seal 90 in that resistance to withdrawal of retractable needle 40 effectively reduces as cross-sectionally tapered body 42 is withdrawn through needle seal 90.

Sealing body 91 has annular ribs 93A, 93B, 93C that co-operate with inside wall 18 of barrel 11 to facilitate improved sealing performance and prevent inadvertent leakage of fluid contents.

Ejector member 92 comprises annular base 921, flange 922, barrel-shaped member 923 and ejector rim 924.

Figure 7:
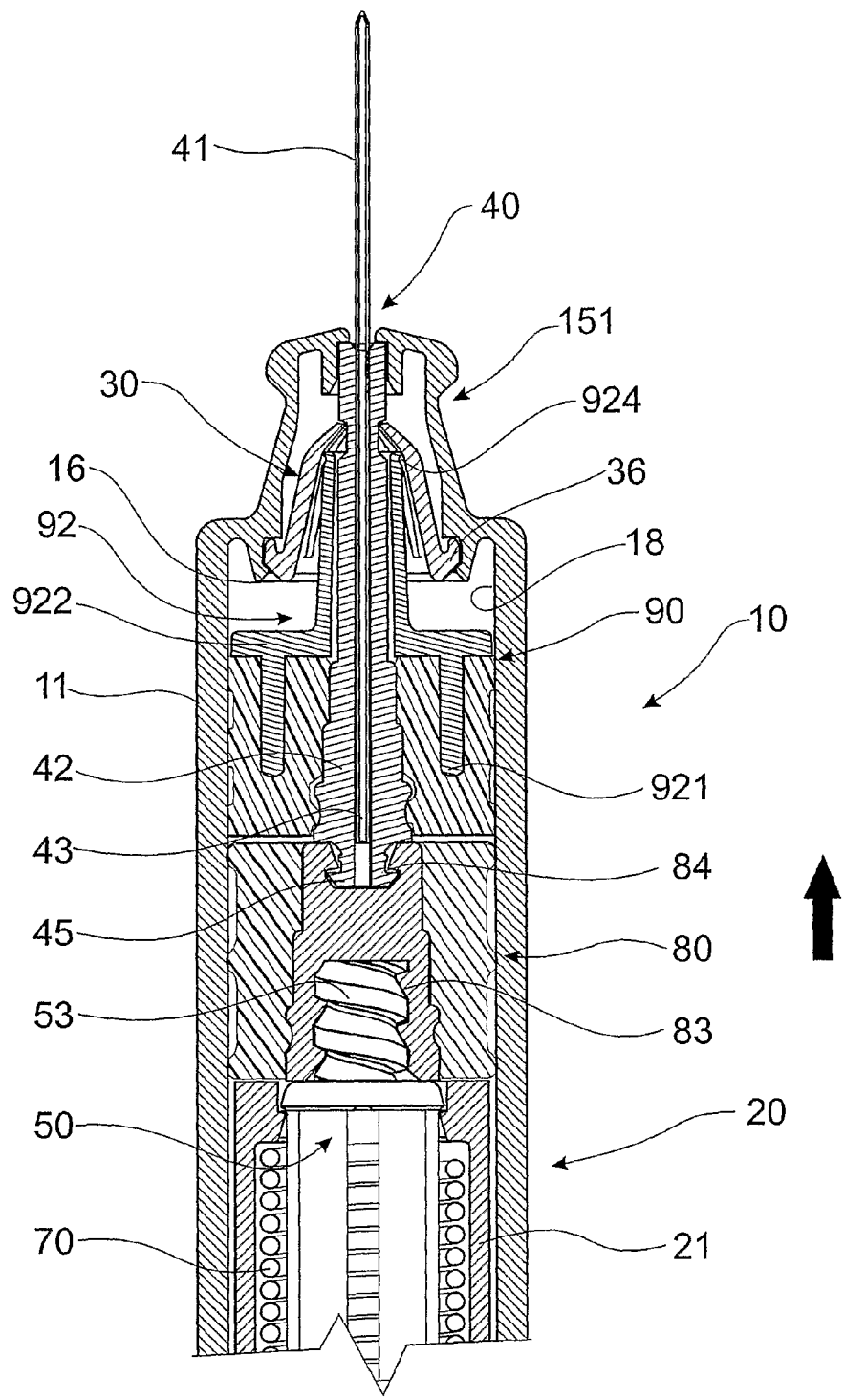
FIG. 7 is a sectional view showing mounting of a retaining member to a barrel and engagement of between inner sealing member and retractable needle prior to retraction.
Figure 8:
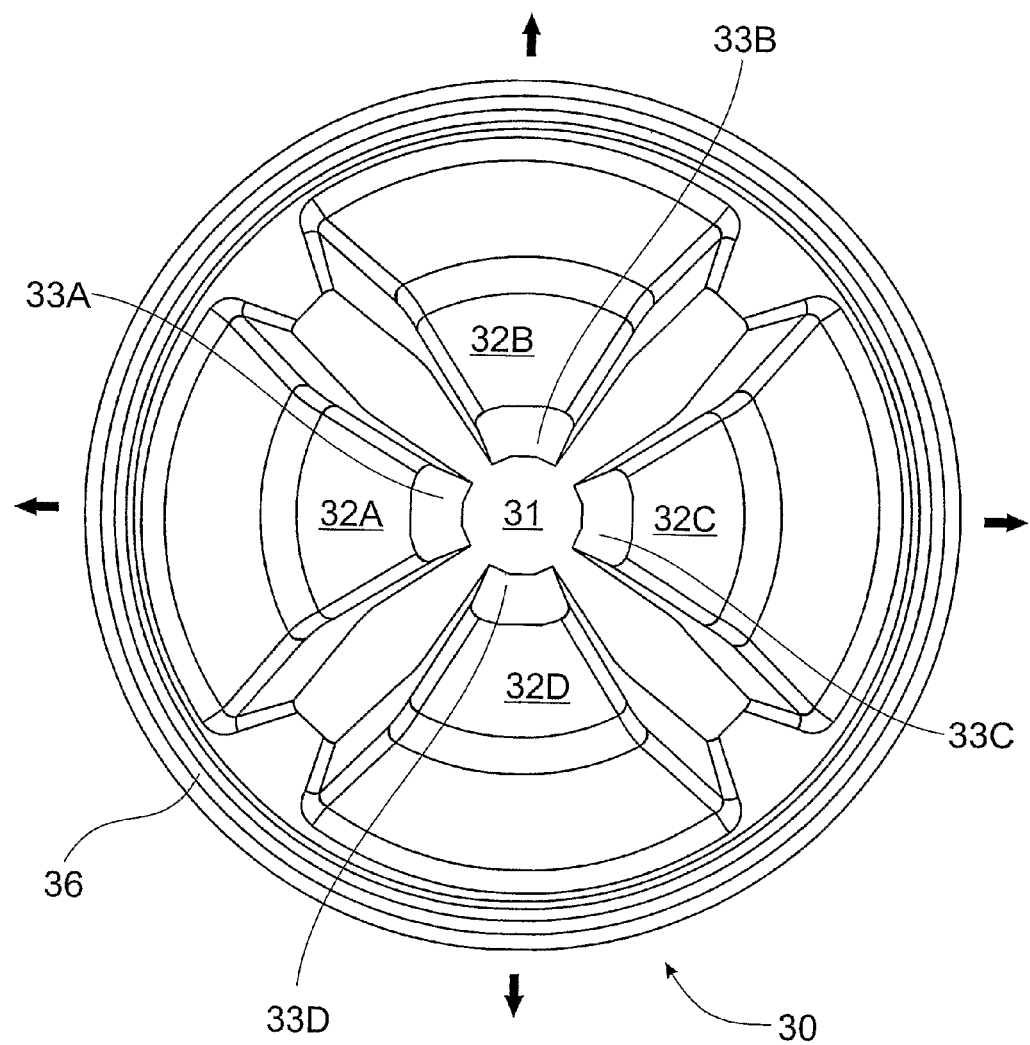
FIG. 8 is a top view of an embodiment of a retaining member.

Referring again to FIG. 6 and also to FIG. 7 and FIG. 8, retaining member 30 covers ejector member 92 so that retractable needle body 42 and cannula 41 protrudes through central bore 31 of retaining member 30. As best seen in FIG. 7, retaining member 30 preferably comprises ledge 36 to hold retaining member 30 in barrel by engaging shoulder 16 located on inside wall 18 at needle end 15 of barrel 11. This mounting configuration is particularly suitable for assembly of syringe 10 when formed of a relatively brittle (i.e "glass-like") plastic, such as typically would be used in the manufacture of a pre-filled syringe 10.

Fingers 32A, 32B, 32C, 32D respectively comprise tapered faces 33A, 33B, 33C, 33D that sit behind underside 49 of head 44 of retractable needle body 42 to hold retractable needle 40 in position during operation of syringe 10. Head 44 of retractable needle body 42 also acts to support cannula 41.

In FIG. 6 and FIG. 7, ejector member 92 of needle seal 90 is symmetric (e.g. annular), so that assembly of the syringe is simplified by obviating the need to align ejector member 92 with fingers 32A, 32B, 32C, 32D of retaining member 30. Prior to retraction of retractable needle body 42 and cannula 41, ejector rim 924 of ejector member 92 abuts fingers 32A, 32B, 32C, 32D of retaining member 30. As shown in FIGS. 7 and 8, ejector member 92 is operable to move further towards needle end 15 of barrel 11 to thereby move or displace fingers 32A, 32B, 32C, 32D of retaining member 30 as indicated by the solid arrows.

Figure 9:
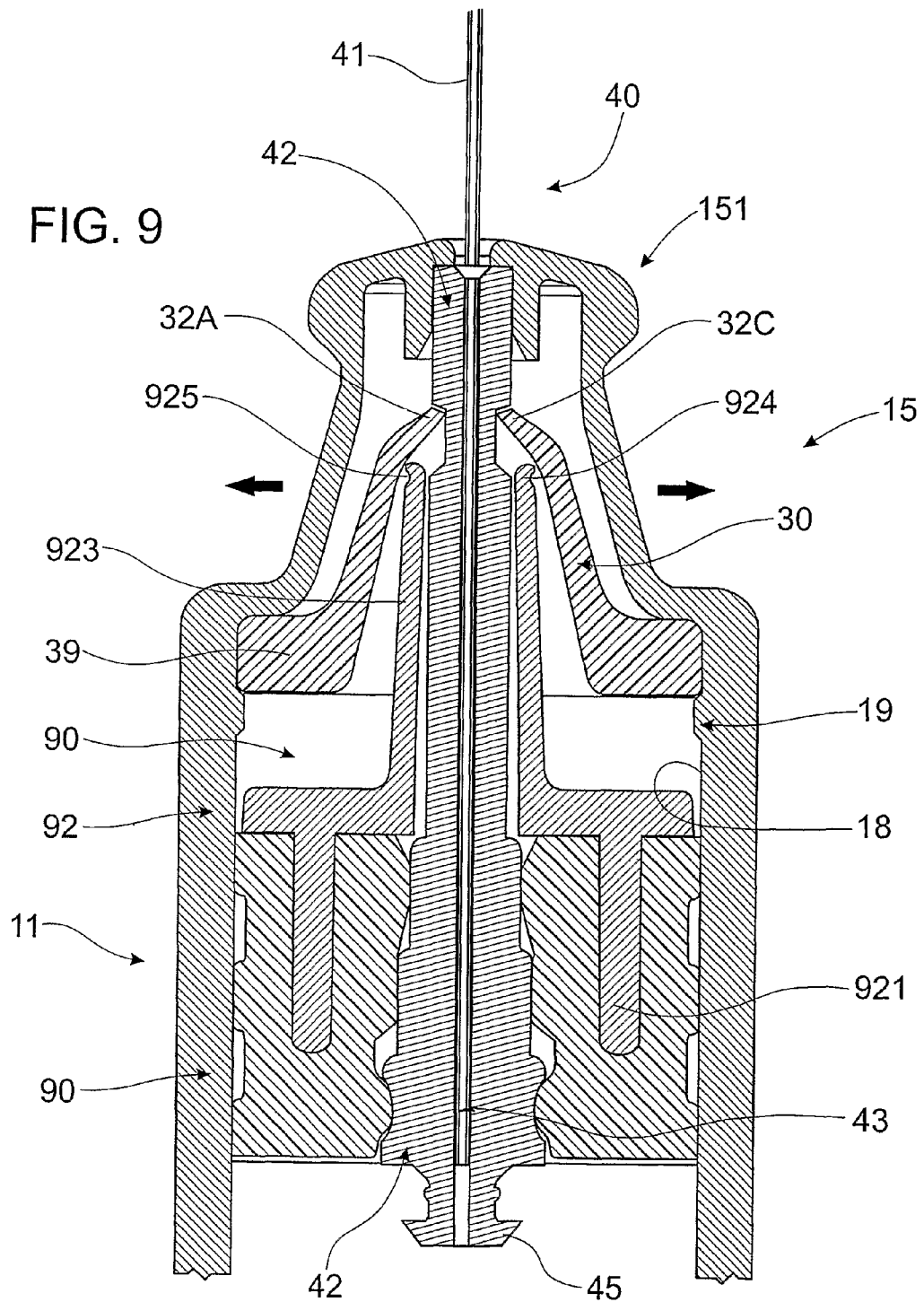
FIG. 9 is a sectional view of an alternative embodiment of a retaining member.

An alternative embodiment of retaining member 30 is shown in FIG. 9, which comprises flanged base or skirt 39 that abuts circumferential shoulder 19 on inside wall 18 at needle end 15 of barrel 11 to thereby hold retaining member 30 in barrel 11. It is noted that groove 925 of ejector rim 924 can engage fingers 32A, 32B, 32C, 32D after ejector member 92 displaces fingers 32A, 32B, 32C, 32D of retaining member 30 as indicated by the solid arrows. In this regard, fingers 32 can resiliently move back into groove 925 and act to prevent any attempt to undo or prevent retraction of needle 40.

The sequence of events that occur to facilitate controlled retraction of needle 40 is as follows.

Typically, syringe 10 is provided prefilled with fluid contents for delivery. Therefore, in this embodiment plunger 20 is provided in an initial position ready for depression to deliver the fluid contents of the syringe 10.

As seen in FIG. 7, at or near the end of plunger 20 depression (indicated by solid arrow), plunger 20 moves plunger seal 80 coupled thereto into the proximity of needle seal 90 at needle end 15 of barrel 11, so that recessed seat 84 of inner seal member 81 receives and snap-lock engages lip 45 of retractable needle body 42. This effectively couples retractable needle 40 to first plunger member 50, as shown in FIG. 7.

Continued movement of plunger 20 in the direction of the solid arrow in FIG. 7 causes three events to occur, essentially simultaneously.

First, plunger seal 80 bears against and forces needle seal 90 further towards needle end 15 of barrel 11 so that ejector rim 924 of ejector member 92 displaces fingers 32A, 32B, 32C, 32D out from behind head 44 of retractable needle body 42, as indicated by the arrows in FIG. 8. This releases retractable needle 40 for subsequent retraction.

Second, plunger housing 21 continues to move toward needle end 15 of barrel 11 so that rim 55 of first plunger member 50 disengages from aperture ledge 23 of plunger housing 21. This disengagement allows compressed spring 70 to decompress and push against base 52 of first plunger member 50 to thereby retract first plunger member 50.

Figure 10:
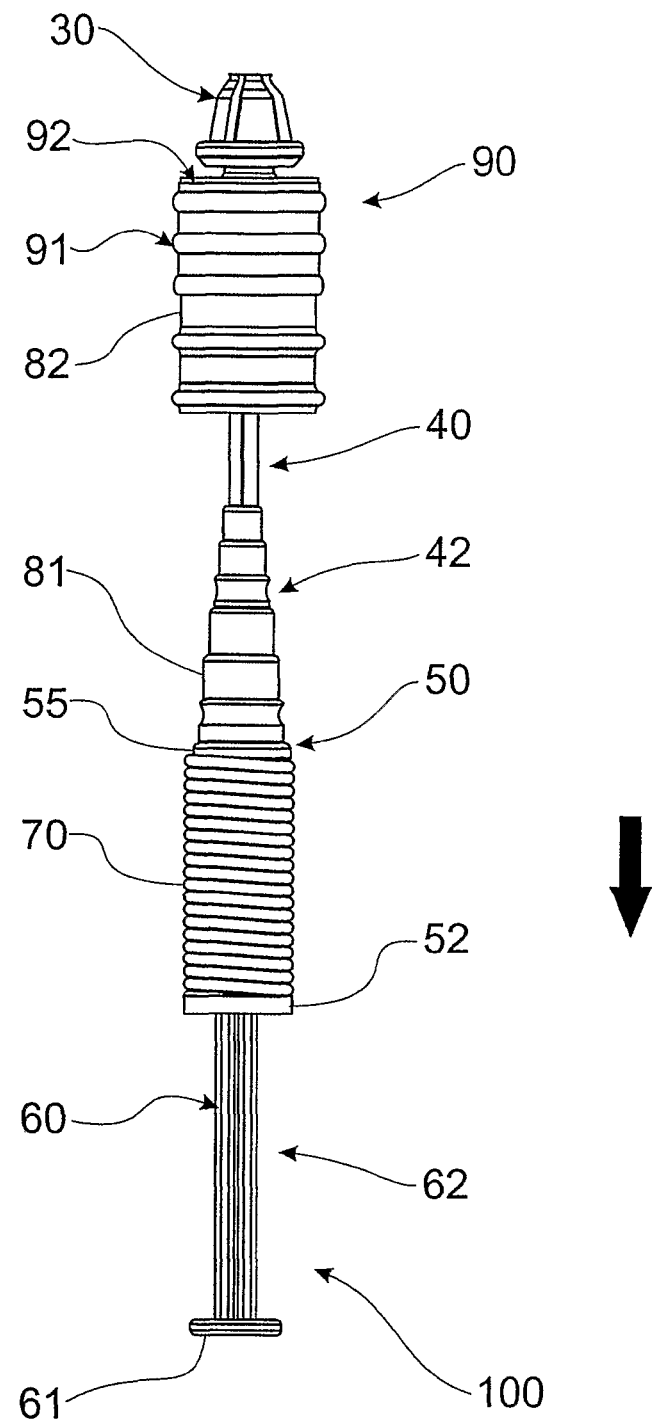
FIG. 10 is a side view of a plunger member and retractable needle during retraction.

Third, inner seal member 81 uncouples from outer sealing member 82, and retractable needle 40, which is coupled to inner sealing member 81, retracts in the direction of the arrow in FIG. 10 (inside plunger housing 21 which remains stationary relative to barrel 11).

Accordingly, control rod 60 retracts, the rate of which retraction is controlled by a user relaxing pressure (such as by way of thumb pressure) against control button 61 of controlling means 62.

Retraction is complete when base 52 of first plunger member 50 abuts plug member 28.

Figure 11:
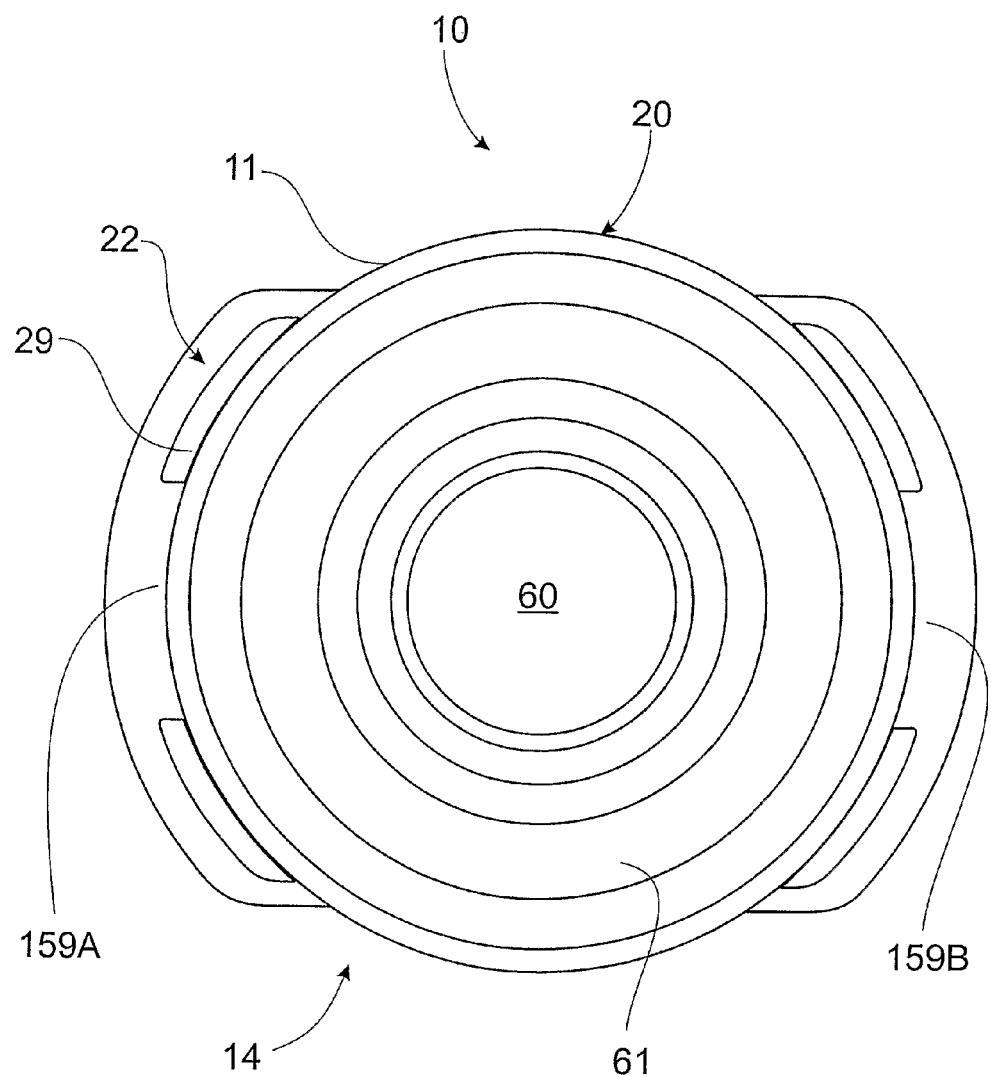
FIG. 11 is a bottom view of a syringe at the end of plunger depression showing the plunger engaged by clips in a barrel.

As shown in FIG. 11, at the end of plunger 20 depression to complete injection of fluid contents of syringe 10, flanged rim 29 of button 22 is locked under clips 159A, 159B at plunger end 14 of barrel 11 and remains locked in that position from thereafter. This also facilitates ease of removal of control rod 60.

Figure 12:
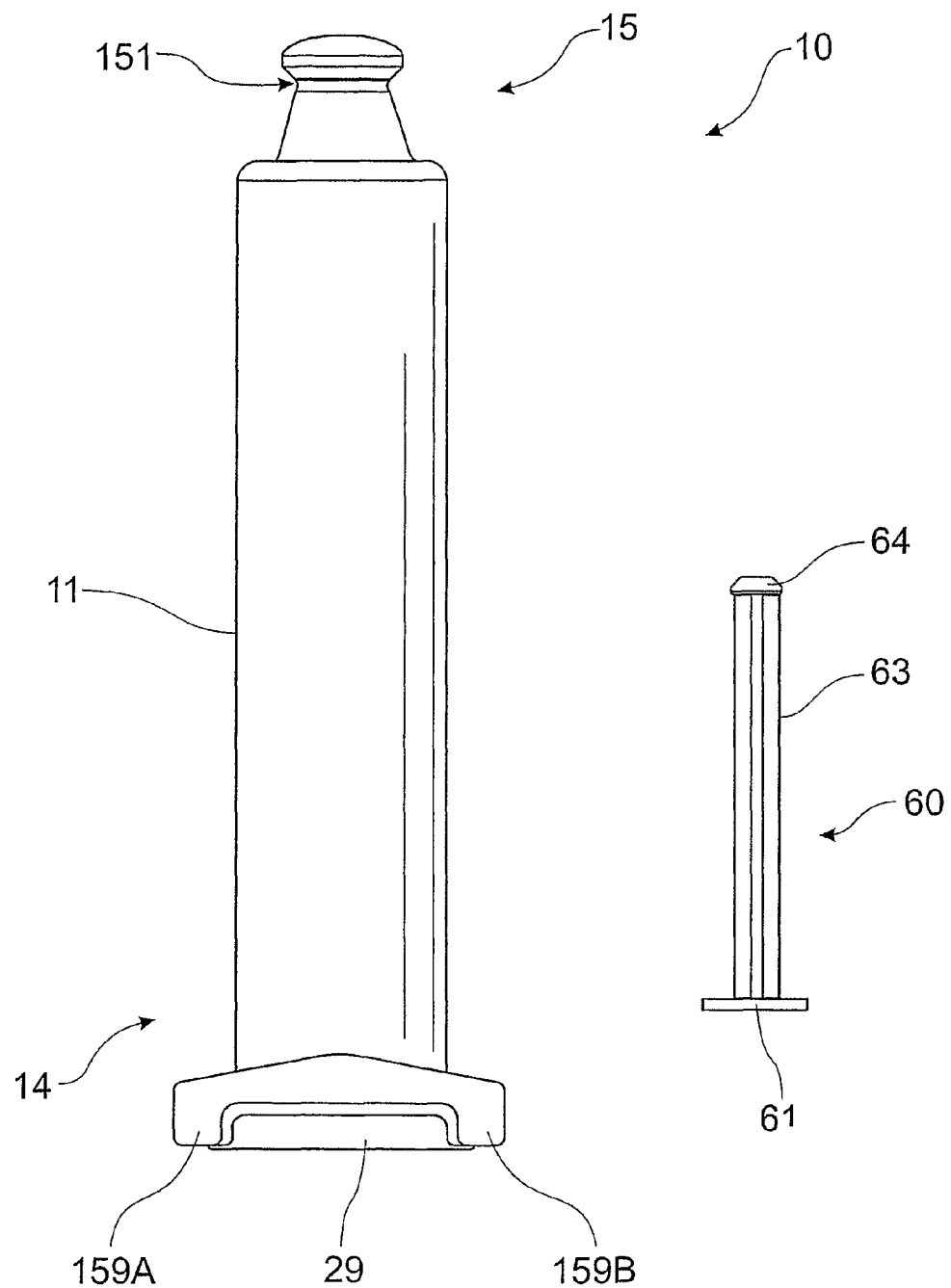
FIG. 12 is a side view of a barrel after completion of needle retraction with control rod detached.

As shown in FIG. 12, at the end of retraction of plunger member 50 and retractable needle 40, control rod 60 can be manually removed from syringe 10 by disengaging ribbed member 64 from nubs 54A, 54B, 54C, 54D in cavity 58 of plunger member 50 (see FIG. 3). Control rod 60 may be discarded as "clean" waste, leaving syringe 10 with plunger 20 remaining inside barrel 11 for a more compact medical waste disposal.

In this regard, it should be noted that engagement of lip 45 by recessed seat 84 of inner seal member 81 seals off cannula 41 to help eliminate blood splatter.

Figure 13:
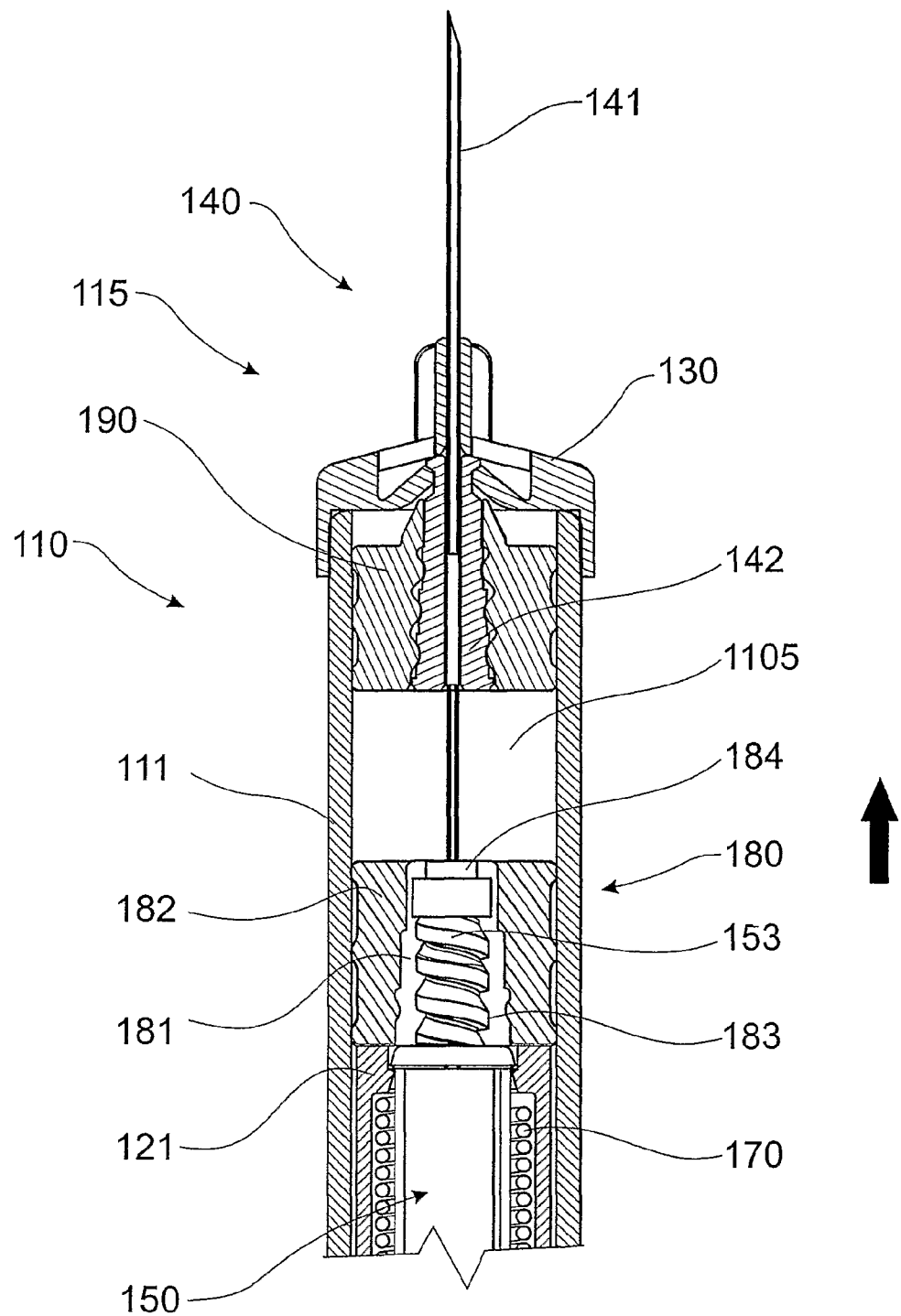
FIG. 13 is a sectional view of an alternative embodiment of a retaining member mounted to a syringe barrel.
Figure 14:
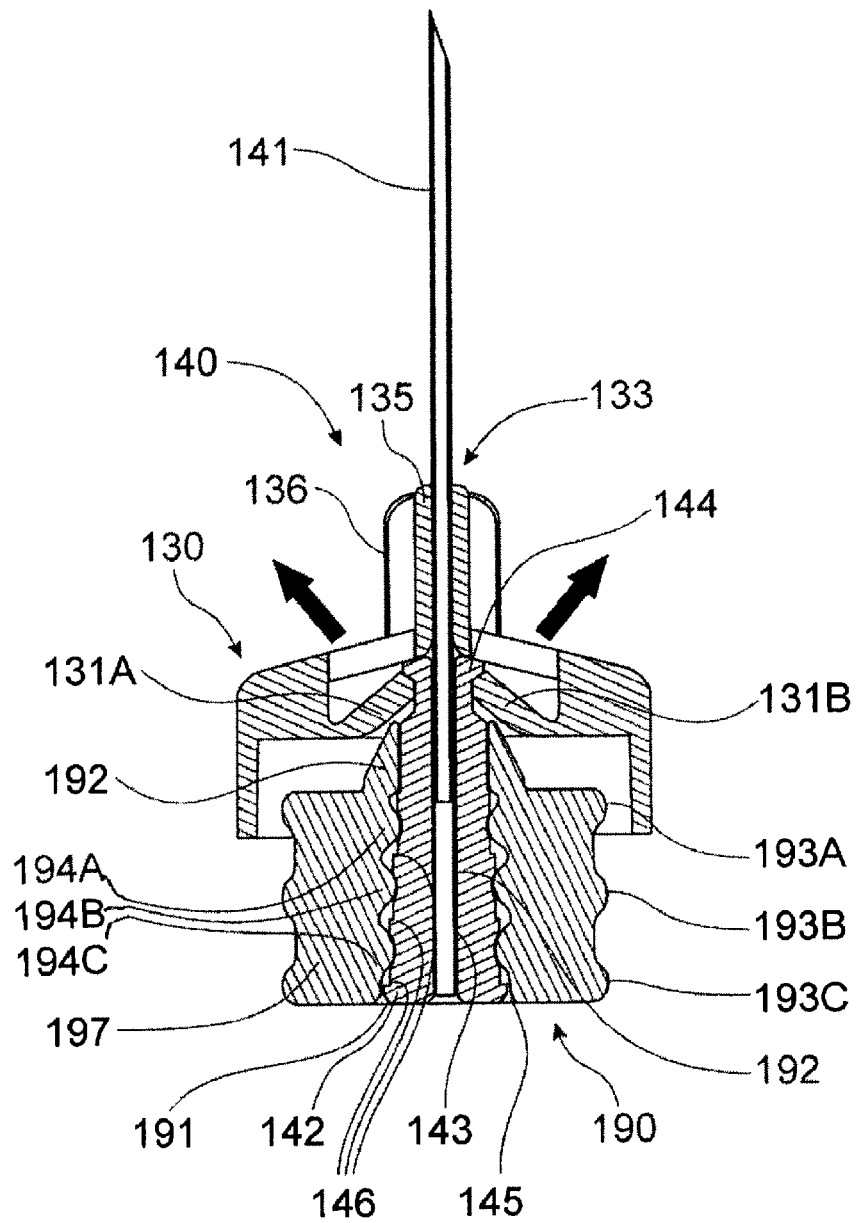
FIG. 14 is a sectional view of an alternative embodiment of a retaining member and sealing means.

Referring now to an alternative embodiment of syringe 110 shown in FIGS. 13 and 14, first plunger member 150 comprises projection 153, which in this embodiment is screw threaded. Plunger seal 180 comprises inner seal member 181 and outer seal member 182 mounted to plunger member 150 to thereby provide a fluid seal between plunger member 150 and barrel 110. Projection 153 of plunger member 150 is coupled to inner seal member 181 by way of plunger engaging means 183 in the form of a complementary screw thread in inner seal member 181. Fluid space 1105 is defined between plunger seal 180, needle mount 190 and needle body 142.

Retractable needle 140 comprises retractable needle body 142 comprising bore 143 and cannula 141. Retaining member comprises cap 130 which is mounted at needle end 115 of barrel 111 and covers sealing body 197 of needle mount 190 so that retractable needle body 142 and cannula 141 protrudes through central bore 133 of cap 130. Cap 130 further comprises sheath mount 136 to which can be mounted a sheath (not shown) for cannula 141. Initially, fingers 131A, 131B sit behind head 144 of retractable needle body 142. Retractable needle body 142 is supported by elongate boss 135 of cap 130 which also prevents retractable needle 140 being forced outwards from cap 130. As in previous embodiments, needle mount 190 comprises sealing body 191 that comprises plurality of complementary steps 194A, 194B, 194C and annular ribs 193A, 193B, 193C. Needle mount ejector member 192 is symmetric (e.g. annular), so that assembly of the syringe is simplified by obviating the need to align ejector member 192 with fingers 131A, 131B of cap 130.

Controlled retraction of retractable needle 140 is essentially as previously described, although with the following differences.

At or near the end of plunger 120 depression in the direction of the solid arrow in FIG. 13, plunger 120 moves sealing means 180 coupled thereto into the proximity of sealing body 197 of needle mount 190 at needle end 115 of barrel 111 to eventually bear against and force needle mount 190 further towards needle end 115 of barrel 111 so that ejector member 192 eventually displaces fingers 131A, 131B out from behind head 144 of retractable needle body 142, as indicated by the solid arrows in FIG. 14. This simultaneously causes inner seal member 181 to disengage from outer sealing member 182 after engaging retractable needle body 142 for subsequent retraction. This occurs as outer sealing member 182 separates from inner sealing member 181, thereby forcing disengagement of lip 145 of retractable needle body 142 from needle mount 190, to allow recessed seat 184 to receive and engage lip 145 of retractable needle body 142. This effectively couples retractable needle 140 to first plunger member 150, essentially as previously shown in FIG. 7.

As previously described, plunger housing 121 continues to move toward needle end 115 of barrel 111 so first plunger member 150 disengages from plunger housing 121. This disengagement allows compressed spring 170 to decompress to thereby retract first plunger member 150 and retractable needle 140 engaged therewith inside plunger housing 121. As previously described, control rod 160 retracts, the rate of which retraction is controlled by a user.

Figure 15:
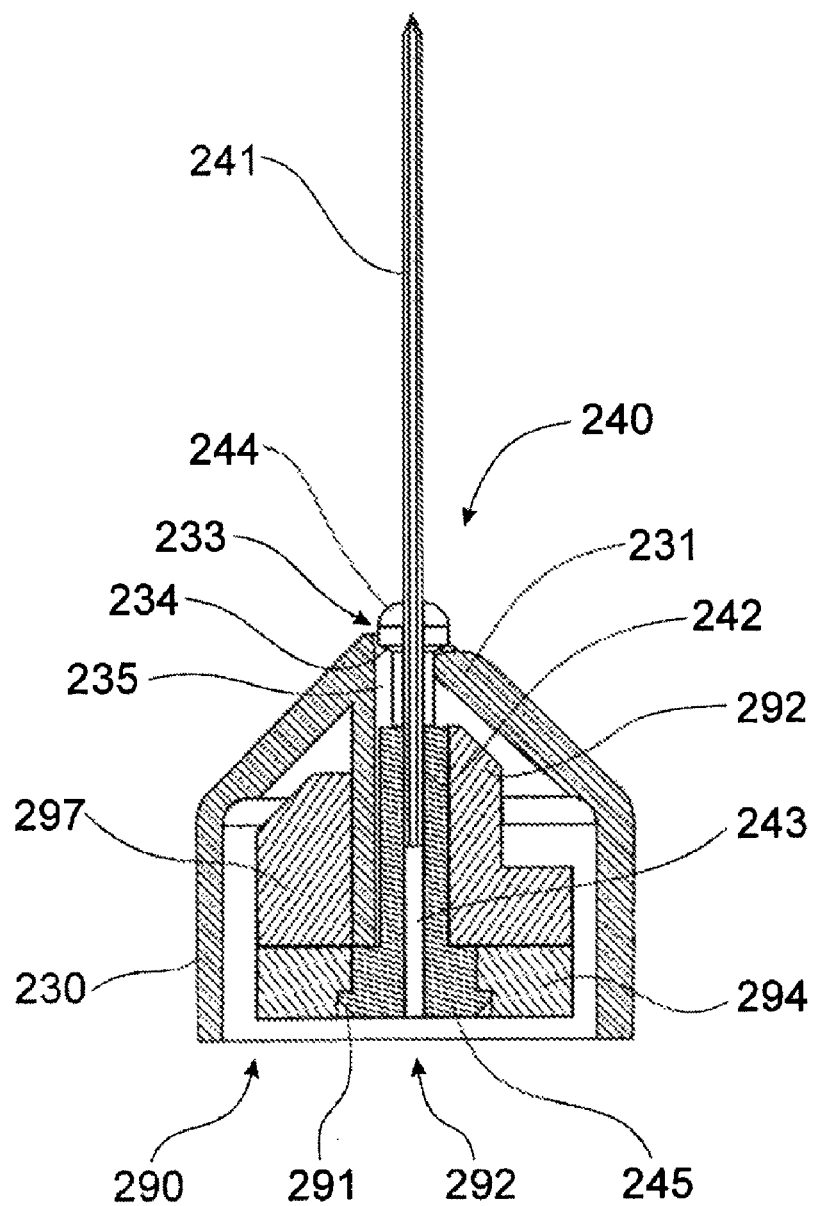
FIG. 15 is a sectional view of another alternative embodiment of a retaining member.

Referring now to another alternative embodiment shown in FIG. 15, wherein retractable needle 240 comprises cannula 241 comprising bore 243, mounted to body 242. Cap 230 may comprise single finger 231 sitting behind head 244 of retractable needle body 242 to prevent inadvertent withdrawal of retractable needle 240 into barrel 211 of syringe 210. Needle body 242 is supported by boss 235 of cap 230.

It is also envisaged that cap 230 may comprise bosses to support the needle body (not shown).

Again referring to FIG. 15, although the stepped configuration of FIGS. 4 and 6 is preferred, it is not essential. In an alternative to the embodiment shown in FIG. 14, retractable needle 240 is initially mounted into central aperture 292 of sealing body 297 of needle mount 290 by way of lip 245 of retractable needle body 242 engaging recess 291 of sealing body 297. In the embodiment shown in FIG. 15, needle mount 290 further comprises sealing member 294 in addition to needle mount sealing body 297. Needle mount sealing body 297 further comprises ejector member 293.

Figure 16:
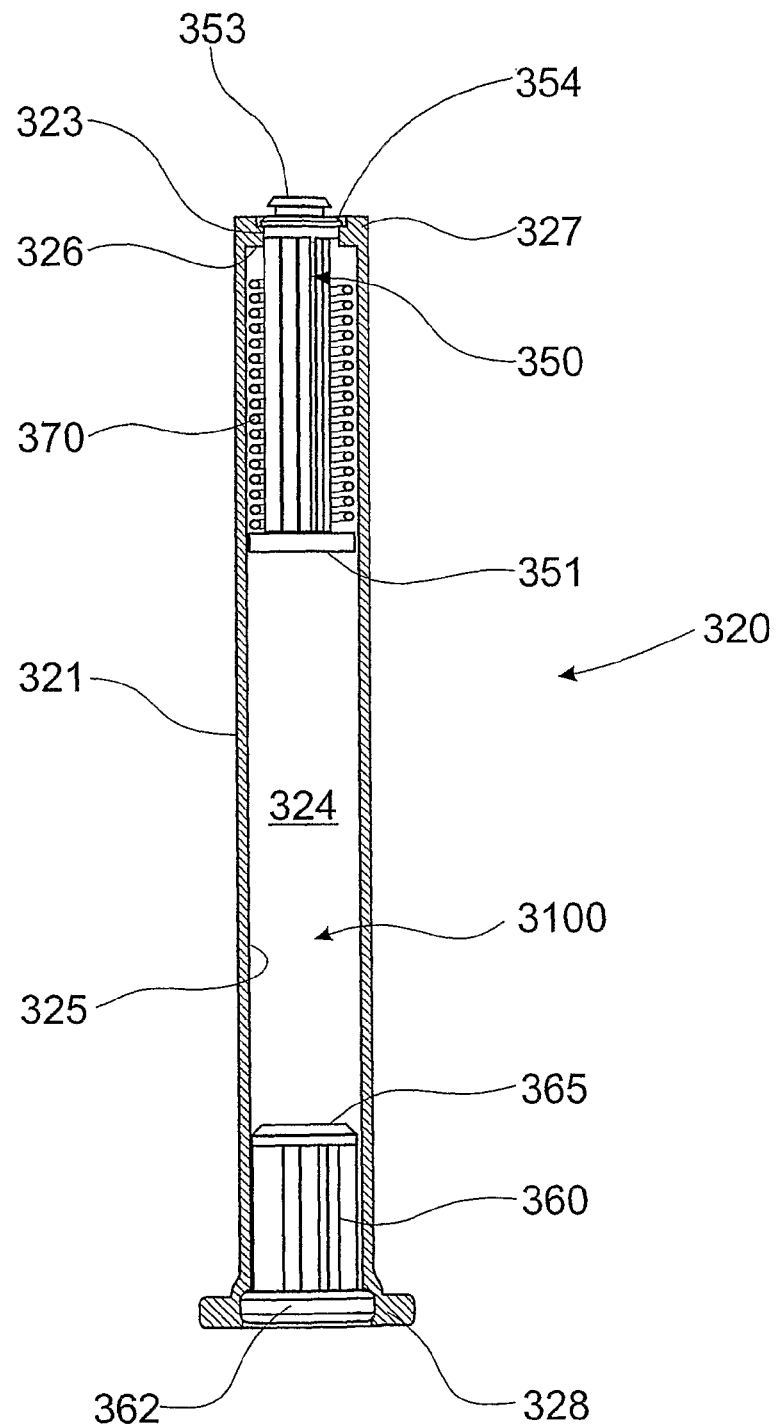
FIG. 16 is a sectional view of an embodiment of a pneumatic controlling means.
Figure 17:
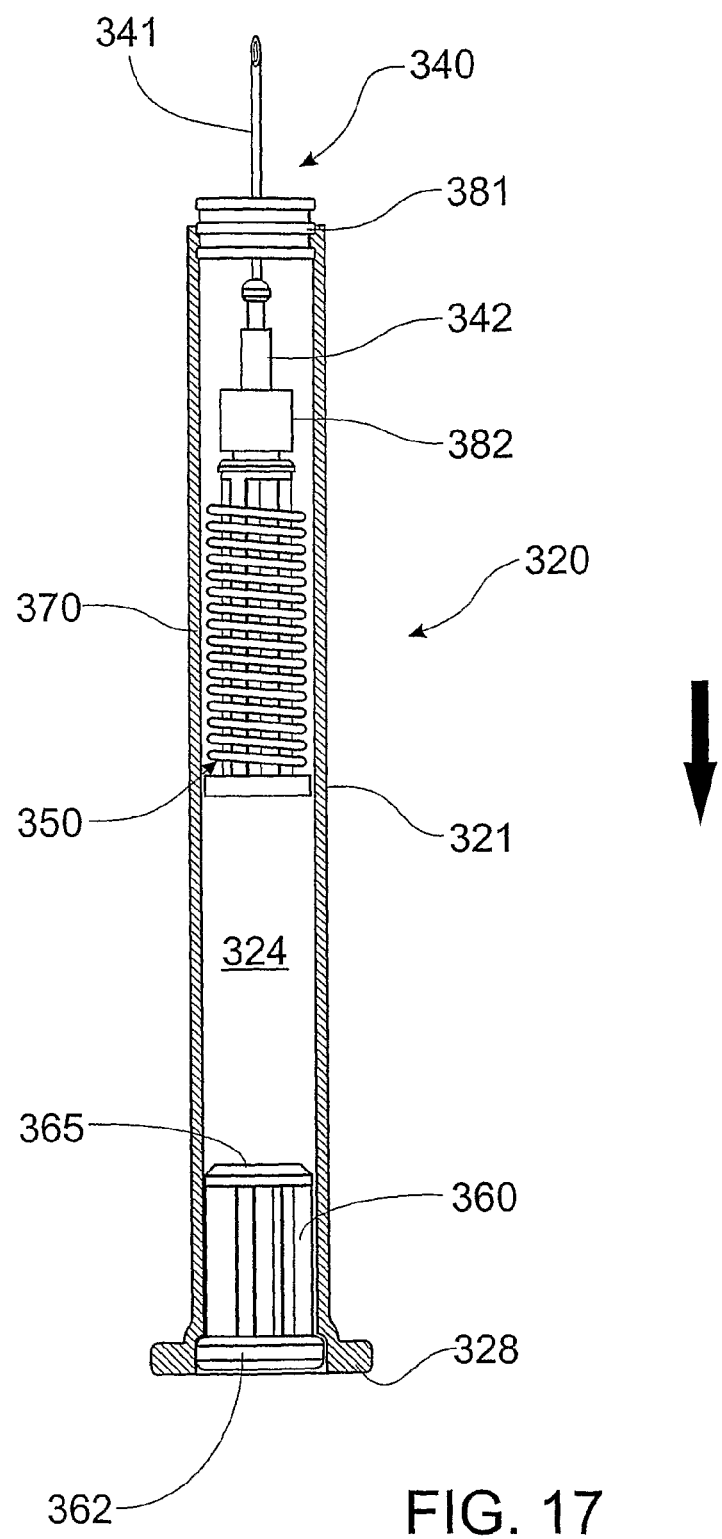
FIG. 17 is a sectional view of an embodiment of a pneumatic controlling means during needle retraction.
Figure 18:
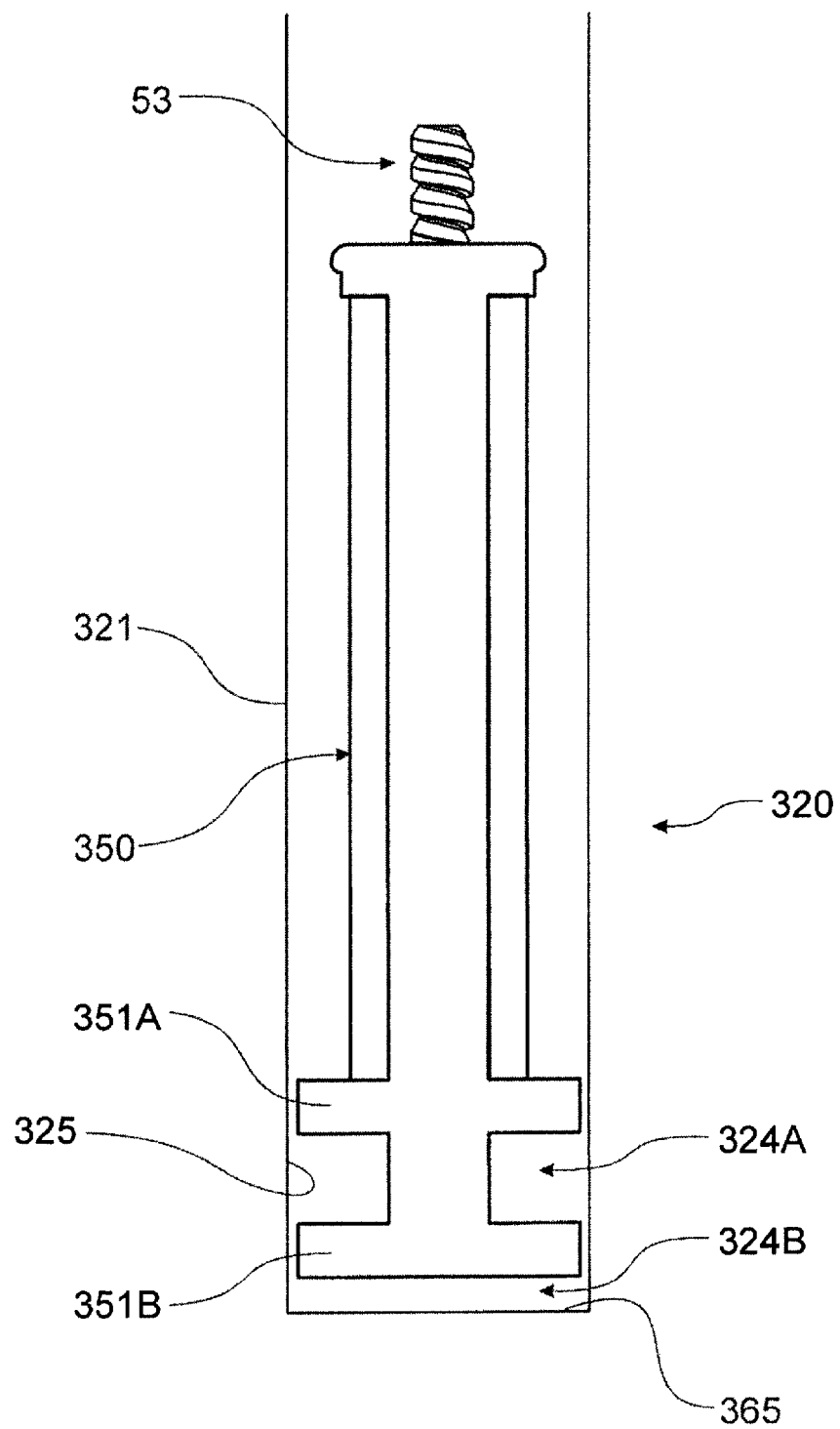
FIG. 18 is a sectional view of another embodiment of a pneumatic controlling means.

It will also be appreciated that the invention contemplates an alternative embodiment of plunger 320 and controlling means 3100, which in this case is pneumatic, as shown in FIGS. 16-18.

Referring to FIG. 16, plunger 320 comprises housing 321 in which is located first plunger member 350 and second plunger member 360 with button 362 fitted into plug member 328, operable by a user. As in previous embodiments and as shown in FIG. 17, sealing means 380 comprises inner sealing member 382 and outer sealing member 381. Retractable needle 340 comprises cannula 341 mounted to body 342.

Plunger 320 further comprises controlling means 3100, which in this embodiment is air-filled space 324 defined by ledge 351 of first plunger member 350, needle end 365 of second plunger member 360 and inner wall 325 of plunger housing 321.

It will be appreciated that fluid-filled or pneumatic controlling means 3100 may comprise any fluid-filled volume 324, wherein typically the fluid is air, that partially resists retraction of first plunger member 350 within plunger housing 321.

Biasing means, in this embodiment compressed spring 370, is mounted to first plunger member 350, held between ledge 351 first plunger member 350 and circumferential shoulder 326 of inner wall 325 of plunger housing 321.

First plunger member 350 further comprises projection 353, which in this case is a snap-lock projection but could alternatively be screw-threaded (as previously described and also as shown in FIG. 18), and rim 354 distal to ledge 351. When assembled, rim 354 fits into recess 327 of plunger housing 321 by way of an interference fit to aperture 323 so that compressed spring 370 cannot force first plunger member 350 out of engagement with plunger housing 321.

At or near the end of plunger 320 depression to deliver fluid contents of the syringe, plunger 320 engages retractable needle 340 as hereinbefore described. First plunger member 350 disengages from aperture 323 of plunger housing 321 to push against ledge 351 of first plunger member 350 and thereby retract first plunger member 350 and retractable needle 340 engaged therewith inside plunger housing 321, in the direction of the solid arrow in FIG. 17. Fluid-filled or pneumatic space 324 within housing 321 defined by ledge 351 of first plunger member 350, needle end 365 of second plunger member 360 and inner wall 325 of plunger housing 321, acts as a pneumatic cushion to regulate the speed at which first plunger member 350 retracts. Essentially, as first plunger member 350 retracts, air-filled space 324 decreases in volume (compared to that before retraction as shown in FIG. 16) but the rate at which air escapes is limited, so that the momentarily compressed air in space 324 acts to limit the rate of retraction of first plunger member 350 and retractable needle 340. This rate of air escape can be regulated by providing one or more apertures (not shown) in needle end 365 of second plunger member 360 to reduce air resistance, or an O-ring or lip (not shown) that fits against inner wall 325 of plunger housing 321 to create greater resistance to, and regulation of, first plunger member 351 retraction.

An example of a modification of the rate of air escape is shown in FIG. 18. First plunger member 350 has paired ledges 351A and 351B, so that controlling means 3100 comprises first air-filled space 324A together with second air-filled space 324B between needle end 365 of second plunger member 360 and inner wall 325 of plunger housing 321, to thereby further assist regulated retraction of first plunger member 350.

In light of the foregoing it will be appreciated that the present invention provides a relatively simple, robust and inexpensive syringe that is automatically disabled with little or no assistance from the user to thereby prevent, or at least minimize the likelihood of, re-use of the syringe.

Furthermore, by controlling or regulating the rate of needle retraction, the likelihood of blood splattering is reduced thereby improving the "user-friendliness" and commercial appeal of the retractable syringe.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A plunger for a syringe having a retractable needle, said plunger comprising a plunger member capable of engaging said retractable needle, a plunger housing; an initially compressed spring, wherein decompression of said spring facilitates needle retraction, and a controlling means initially internally located within said plunger housing and releasably engaged by said plunger member, which facilitates control of the rate of retraction of said plunger member and said retractable needle when engaged with said plunger member and which controlling means is disengageable from said plunger member following delivery of fluid contents of said syringe, wherein the controlling means has a first end configured to engage the plunger member, and a second end configured to enable control over the rate of retraction of the retractable needle.

2. The plunger of claim 1, wherein the controlling means comprises a control member which is disengageable from said plunger member.

3. The plunger of claim 2, wherein the control member is a control rod.

4. A syringe having a barrel, a retractable needle and a plunger, said plunger comprising a plunger member engageable with said retractable needle, a plunger housing; an initially compressed spring, wherein decompression of said spring facilitates needle retraction, and a controlling means initially internally located within said plunger housing and releasably engaged by said plunger member, which controlling means facilitates control of the rate of retraction of said plunger member and said retractable needle when engaged with said plunger member and which controlling means is disengageable from said plunger member following delivery of fluid contents of said syringe, wherein the controlling means has a first end configured to engage the plunger member, and a second end configured to enable control over the rate of retraction of the retractable needle.

5. The syringe of claim 4, wherein the controlling means comprises a control member which is disengageable from said plunger member.

6. The syringe of claim 5, wherein the control member is a control rod.

7. The syringe of claim 4 further comprising a retaining member for facilitating initial retention of said retractable needle at a needle end of said barrel.

8. The syringe of claim 7, which further comprises an ejector member operable to release said retractable needle from said retaining member to thereby allow retraction of said retractable needle when delivery of fluid contents of said syringe is complete.

9. The syringe of claim 8, wherein said ejector member does not require alignment with said retaining member to release said retractable needle from said retaining member.

10. The syringe of claim 4, wherein the syringe comprises a sealing means that comprises an inner sealing member and an outer sealing member.

11. The syringe of claim 10, wherein said inner sealing member has a tapered cross section and comprises a plurality of annular steps that engage complementary annular ribs inside said outer seal member.

12. The syringe of claim 4, wherein said retractable needle comprises a cannula and a needle body.

13. The syringe of claim 12, wherein said needle body has a tapered cross section, tapering toward said cannula, and comprises a plurality of steps.

14. The syringe of claim 13, wherein said needle body is mounted to a needle mount that is located in said barrel.

15. The syringe of claim 14, wherein said needle mount comprises a plurality of complementary steps that respectively receive said plurality of steps of said needle body.

16. The syringe of claim 4, which is a prefilled syringe.

17. A prefilled syringe having a barrel; a retractable needle; a plunger comprising a housing and a plunger member engageable with said retractable needle; a spring initially compressed within said plunger; a needle seal located inside said barrel to which is mounted said retractable needle; and a retaining member to facilitate initial retention of said retractable needle at a needle end of said barrel; arranged so that decompression of said spring facilitates retraction of said plunger member and said needle when engaged with said plunger member and wherein said plunger further comprises a controlling means which facilitates control of the rate of retraction of said plunger member and said retractable needle when engaged with said plunger member, wherein the controlling means has a first end configured to engage the plunger member, and a second end configured to enable control over the rate of retraction of the retractable needle, and which controlling means is disengageable from said plunger following delivery of fluid contents of said syringe.

18. A plunger for a syringe having a retractable needle, said plunger comprising a plunger housing, a first plunger member engageable with said retractable needle and a second plunger member, which co-operate to form a pneumatic controlling means including an initially compressed spring that decompresses to facilitate retraction of the retractable needle, and which pneumatic controlling means facilitates control of the rate of retraction of said first plunger member and said retractable needle when engaged with said first plunger member.

19. The plunger of claim 18, wherein the syringe is a prefilled syringe.

20. A syringe having a barrel; a retractable needle and a plunger comprising a plunger housing, a first plunger member engageable with said retractable needle and a second plunger member, which co-operate to form a pneumatic controlling means including an initially compressed spring that decompresses to facilitate retraction of the retractable needle, and which pneumatic controlling means facilitates control of the rate of retraction of said first plunger member and said retractable needle when engaged with said first plunger member.

21. The syringe of claim 20, which is a prefilled syringe.

22. A prefilled syringe having a barrel; a retractable needle; a plunger comprising a first plunger member engageable with said retractable needle, a second plunger member and a housing; a spring initially compressed within said plunger; a needle seal located inside said barrel to which is mounted said retractable needle; and a retaining member to facilitate initial retention of said retractable needle at a needle end of said barrel; arranged so that decompression of said spring facilitates retraction of said needle and wherein said plunger further comprises a pneumatic controlling means which facilitates control of the rate of retraction of said first plunger member and said retractable needle when engaged with said first plunger member.

* * * * *